US006251596B1

(12) United States Patent
Cook et al.

(10) Patent No.: US 6,251,596 B1
(45) Date of Patent: Jun. 26, 2001

(54) ASPERGILLUS N-MYRISTOYL TRANSFERASE GENES AND POLYEPTIDES AND USES THEREOF

(75) Inventors: W. James Cook, Natick; Christine E. Bulawa, Arlington, both of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/163,444

(22) Filed: Sep. 30, 1998

(51) Int. Cl.[7] ....................................................... C12Q 1/68
(52) U.S. Cl. ........................... 435/6; 435/91.1; 435/252.1; 435/320.1; 536/23.1; 536/24.3
(58) Field of Search .......................... 435/6, 91.2, 320.1, 435/252.1; 536/23.1, 24.3

(56) References Cited

PUBLICATIONS

Georgie et al, Result #19, accession #V58329, Us patent 5807732A, 1995.*
Parang et al., Arch. Pharm. Pharm. Med. Chem. vol. 329, pp. 475–482, Nov. 1996.*
Lodge et al.; Comparison of Myristoyl–CoA:Protein N–Myristoyltransferses from Three Pathogenic Fungi: *Cryptococcus neoformans, Histoplasma capsulatum*, and *Candida albicans*; J. of Bio. Chem. 269/4:2996–3009; 1994.
Weinberg et al.; "Genetic studies reveal that myristoylCoA: protein N–myristoyltransferase is an essential enzyme in *Candida albicans*", Molecular Microbiology 16/2:241–250; 1995.
Lodge et al.; "Targeted gene replacement demonstrates that myristoyl–CoA:protein N–myristoyltransferace is essential for viability of *Cryptococcus neoformans*"; Proc. Natl. Acad. Sci. USA 91:12008–12012; 1994.
Lodge et al.; "Genetic and Biochemical Studies Establish that the Fungicidal . . . (NMT) is Nmt–dependent"; J. Biol. Chem 273/20: 12482–12491, 1998.
Stone et al.; "N–myristoylation is required for function of the pheromone–responsive . . . N–myristoyl transferase"; Genes & Development 5:1969–1981; 1991.

\* cited by examiner

*Primary Examiner*—Lisa B. Arthur
*Assistant Examiner*—Jehanne Souaya
(74) *Attorney, Agent, or Firm*—Fish & Richardson, PC

(57) ABSTRACT

Disclosed is an *Aspergillus fumigatus* N-myristoyltransferase gene and its use in identifying antifungal agents, for example.

42 Claims, 5 Drawing Sheets

Aspergillus fumigatus NMT

```
  1 ATGGCGGAGTCGCTATTGGAAAACAACCCGCTCCAGGAACGAGACGGCCATGGACAAGGACAAGGCGGCGGAGGCAATGCGCAAATGAACATTG   100
    M  A  E  S  L  L  E  N  N  P  A  L  R  N  E  T  A  G  M  D  K  D  K  A  A  E  A  M  R  K  M  N  I  A

101 CCGAATTGCTGACAGGCTTGTCAGTTTCCGGGAAGAACCAGAAGGATATGGCTTCGTACAAGTTTTGGCAAACGCAGCCTGTGCCCCGATTCGATGAGAC   200
    E  L  L  T  G  L  S  V  S  G  K  N  Q  K  D  M  A  S  Y  K  F  W  Q  T  Q  P  V  P  R  F  D  E  T

201 GAGTACCGATACTGGGGGCCCTATCAAGATCATTGATCCTGAAAAGGTCTCAAAGGAACCGGATGCGCTGCTTGAAGGATTTGAATGGGCACACTCGAC   300
    S  T  D  T  G  G  P  I  K  I  I  D  P  E  K  V  S  K  E  P  D  A  L  L  E  G  F  E  W  A  T  L  D

301 CTGACAAACGAGACTGAGCTGCAGGAGCTGTGGGATTTGTTGACGTATCACTACGTAGAGGACGACAATGCCATGTTCCGGTTCAGATATTGCAGTCGT   400
    L  T  N  E  T  E  L  Q  E  L  W  D  L  L  T  Y  H  Y  V  E  D  D  N  A  M  F  R  F  R  Y  S  Q  S  F

401 TCCTACACTGGGCTCTTATGTGCGCTGGTGTCCGCGTGACATGTCGGCTACGAAGTCGGCAAACTGGTAGCGTCCATTTGCGGTGT   500
    L  H  W  A  L  M  S  P  G  W  K  K  E  W  H  V  G  V  R  A  T  K  S  R  K  L  V  A  S  I  C  G  V

501 CCCGACAGAGATCAATGTGCGCAATCAAAGCTCAAGGTCGTCGAGATCAATTCCTCTGCATCCACAAGAAGCTCCGTCGAAGCGTTGACCCCAGTT   600
    P  T  E  I  N  V  R  N  Q  K  L  K  V  V  E  I  N  F  L  C  I  H  K  K  L  R  S  K  R  L  T  P  V

601 CTCATCAAAGAAATCACCCGTCGTTGCTACCTCAATGGCATCATCTACCAAGCCATTTACACTGCGGGTGTGGTGCTCCCCACTCCTGTCAGCTGCCGCT   700
    L  I  K  E  I  T  R  R  C  Y  L  N  G  I  I  Y  Q  A  I  Y  T  A  G  V  V  L  P  T  P  V  S  S  C  R  Y
```

FIG. 1A

```
701  ACTACCACCGTCCTCTTGGACTGGTTGAAGCTTTACGAGGTCGGCTTCTCGCCTCTCCCTGCCGATCCACCAAGGCGCCAGATCACCAAGAATCACCT   800
      Y  H  R  P  L  D  W  L  K  L  Y  E  V  G  F  S  P  L  P  A  G  S  T  K  A  R  Q  I  T  K  N  H  L

801  GCCCAGTACTACTCCTACCCCCGTCTTCGCCCCATGGAGCCCAAAGACATTGACACAGTGCATGATCTTTTGCAGCGATACTTGTCGCGGTTTGCGTTG   900
      P  S  T  T  S  T  P  G  L  R  P  M  E  P  K  D  I  D  T  V  H  D  L  L  Q  R  Y  L  S  R  F  A  L

901  AACCAGGCCTTTACGCGAGAGGAAGTGGACCATTGGCTCGTGCACAAGCCGGTGAAAGAGCCAGTCGTCTGGGCATACGTGGTAGAGGACCCTG   1000
      N  Q  A  F  T  R  E  E  V  D  H  W  L  V  H  K  P  E  T  V  K  E  Q  V  V  W  A  Y  V  V  E  D  P  E

1001 AAACGCACAAGATCACCGACTTCTTTTCCTTCTACAACCTCGAATCCACCGTCATTCAGAATCCCAAGCATGACAATGTGCGTGCTGCTTACCTGTACTA   1100
      T  H  K  I  T  D  F  F  S  F  Y  N  L  E  S  T  V  I  Q  N  P  K  H  D  N  V  R  A  A  Y  L  Y  Y

1101 CTATGCAACCGAAACAGCTTTCACCAATAACATGAAGGCTCTCAAAGAGCGTCTGATGCTGATGAATGACGCTCTGATCCTGGCTAAGAAGGCGCAC   1200
      Y  A  T  E  T  A  F  T  N  N  M  K  A  L  K  E  R  L  L  M  L  M  N  D  A  L  I  L  A  K  K  A  H

1201 TTTGATGTGTTCAACGCACTTACGCTTCACGATAACCCTCTGTTCCTCGAACAACTCAAATTTGGAGCTGGCGATGGGCAGCTTCACTTCTACCTCTACA   1300
      F  D  V  F  N  A  L  T  L  H  D  N  P  L  F  L  E  Q  L  K  F  G  A  G  D  G  Q  L  H  F  Y  L  Y  N

1301 ACTATCGCACCGCCCCTGTTCCTGGAGGAGTTAACGAGAAGAACCTGCCGGATGAGAAAGAATGGAGGCGTTGGCATCGTTATGCTGTAA           1392
      Y  R  T  A  P  V  P  G  G  V  N  E  K  N  L  P  D  E  K  R  M  G  G  V  G  I  V  M  L  *

(SEQ ID NO:1)        FIG. 1B
(SEQ ID NO:2)
``` nmt1 (Aspergillus fumigatus)

```
  1  TCCGACTCTAAGGATCGCAAGGGCCCCGAGGGCCAGTCTTCCGAAAAGAAGATGGCGGTGAACATAACCCTCAGATGGCGGAGTCGCTAT  100
     AGGCTGAGATTCCTAGCGTTCCCGTTCCGGGGGCTCCCGGTCAGAGTCTTTCTTTCTACCGGCACTTGTATTGGGAGTCTACCGCTCAGCGATA
  1                                                                 M  A  E  S  L  L            6

101  TGGAAAACAACCCGCTCTCAGGAACAGACGACATGAAGACAAGGCGGCGAGGCAATGCGCAAAATGAACATTGCCGAATTGCTGACAGG      200
     ACCTTTTGTTGGGCGAGAGTCCTTGTCTGCTGTACTTCTGTTCCGCCGCTCCGTTACGCGTTTTACTTGTAACGCTTAACGACTGTCC
  7  E  N  N  P  A  L  R  N  E  T  A  G  M  D  K  D  K  A  A  E  A  M  R  K  M  N  I  A  E  L  L  T  G   39

201  CTTGTCAGTTTCGGGAAGAACCAGAAGGATATGGCTTCGTACAAGTTTTGGCAAACGCAGCCTGTGCCCCGATTCGATGAGACGAGTACCGATACTGGG  300
     GAACAGTCAAAGGCCCTTCTTGGTCTTCCTATACCGAAGCATGTTCAAACCGTTGCGTCGGACACGGGCTAAGCTACTCTGCTACTGGCTATGACCC
 40  L  S  V  S  G  K  N  Q  K  D  M  A  S  Y  K  F  W  Q  T  Q  P  V  P  R  F  D  E  T  S  T  D  T  G   72

301  GGGCCCTATCAAGATCATTGATCCTGAAAAGGTCTCAAAGGAACCGGATGCGCTGCTTGAAGGATTTGAATGGGCGACACTGACCTGACAAAGAGACTG  400
     CCGGGATAGTTCTAGTAACTAGGACTTTTCCAGAGTTTCCTTGGCTACGCGACGAACTTCCTAAACTTACCCGCTGTGACTGGACTGTTGCTCTGAC
 73  G  P  I  K  I  I  D  P  E  K  V  S  K  E  P  D  A  L  L  E  G  F  E  W  A  T  L  D  L  T  N  E  T  E  106

401  AGCTGCAGGAGCTGTGGGATTTGTTGACGTATCACTACGTAGAGATACGACAATGCCATGTTCCGTTCCGGTTCAGATATTCGCAGTCGTTCCTACACTGGTGGT  500
     TCGACGTCCTCGACACCCTAAACAACTGCATAGTGATGCATCTCCTGTCTGTTACGGTACAAGGCTCAAGCGTCAGCAAGGATGTGACCACCA
107  L  Q  E  L  W  D  L  L  T  Y  H  Y  V  E  D  D  N  A  M  F  R  F  R  Y  S  Q  S  F  L  H  W          137

501  GCACAACGCGGCCGAGGGATCGTGTTCTCACCGGCTTGGGAGGGTGTGATTATTTGAGCGCTGACGCGTAGGGCTCTTATGTCGCCTGGCT            600
     CGTGTTGCGCCGGCTCCCTAGACAAAGAGTGGCCGAACCCTCCCACACCTAATAAACTGCGACTGTTAAAACTGCATCCCGAGAATACAGCGGACCGA
138                                            A  L  M  S  P  G  W                                       144
```

```
1301  CATGAAGGCTCTCAAAGAGCGTCTGCTGATGAATGACGCTCTGATCCTGGCTAAGAAGTAATACAGGGATCCACTGCCATTTCCCTGGAGTT    1400
      GTACTTCCGAGAGTTTCTCGCAGACGACTACTGCGAGACTAGGACCGATTCTTCCATTGATGTCCCTAGTGACGGTAAAGGGACCTCAA
378   M  K  A  L  K  E  R  L  L  M  M  N  D  A  L  I  L  A  K  K  A                                 399

1401  GACTTACGAAGCTGACATTGTGTTGATAGGCGCACTTTGATGTGTTCAACGCACTTAGCGTTCACGATAAACCCTGTTCCTGAACAACTCAAATTTGG    1500
      CTGAATGCTTCGACTGTTAACACTATCCGCGTGAAACTACACAAGTTGCCTGAATGCGAAGTGCTATTGGGAGACAAGGAGCTTGTTGAGTTTAAACC
400                    H  F  D  V  F  N  A  L  T  L  H  D  N  P  L  F  L  E  Q  L  K  F  G          422

1501  AGCTGGGCGATGGGCAGCTTCACTTCTACCTTCTACAACTATGCCACCGCCCCTGTTCCTGGAGGAGTTAACGAGAAGAACCTGCCGATGAGAAAGAATG    1600
      TCGACCCGCTACCCGTCGAAGTGAAGATGTTGATACGGTGGCGGGGACAAGGACCTCCTCAATTGCTCTTCTTGGACGGCTACTCTTTTCTTAC
423   A  G  D  G  Q  L  H  F  Y  L  Y  N  Y  R  T  A  P  V  P  G  G  V  N  E  K  N  L  P  D  E  K  R  M    455

1601  GGAGGCGTTGGCATCGTTATGCTCTGTAAAACATTCTCACCGCATGACCATGCCTCTCGCCTCGTTGATGATCGCATCTTATACCTATTTCTCGCTGTGAC    1700
      CCTCCGCAACCGTAGCAATACGACATTTTGTAAGAGTGGCGTACGGCTGTTAAGAGTCGGAGCAACTACTGATCGTAGAATATGGATAAAGAGCGACACTG
456   G  G  V  G  I  V  M  L  *                                                                       463

1701  ATGAATTGGTATGCGAAATACCATGAAAATTTG  1735                (SEQ ID NO:3)
      TACTTAACCCATACGCTTTATGTACTTTTAAAC                     (SEQ ID NO:2)
```

ASPERGILLUS N-MYRISTOYL TRANSFERASE GENES AND POLYEPTIDES AND USES THEREOF

Field of the Invention

The invention relates to N-myristoyl transferase of the fungus *Aspergillus fumigatus* and its use in identifying antifungal agents.

BACKGROUND OF THE INVENTION

The enzyme N-myristoyl transferase (NMT) is responsible for cotranslational modification of a variety of fungal proteins. NMT catalyzes the attachment of a 14-carbon saturated fatty acid to the N-terminal glycine residue of cellular proteins. This modification is thought to be irreversible and essential for the full biological activity of myristoylated proteins.

SUMMARY OF THE INVENTION

The invention is based on the discovery of an NMT gene in the fungus *Aspergillus fumigatus*. The Aspergillus NMT coding sequence is depicted in FIG. 1 as SEQ ID NO:1, with the amino acid sequence represented by SEQ ID NO:2. The NMT genomic sequence is depicted in FIG. 2 as SEQ ID NO:3.

The NMT gene of the invention is essential for survival of Aspergillus. Accordingly, the NMT nucleic acid sequence of the invention, and the NMT polypeptide of the invention, are useful targets for identifying compounds that are inhibitors of Aspergillus. Such inhibitors attenuate fungal growth by inhibiting the activity of the essential NMT polypeptide, or by inhibiting transcription or translation. Accordingly, in one aspect, this invention provides isolated nucleic acid molecules encoding Aspergillus NMT polypeptides or biologically active portions thereof, as well as nucleic acid fragments suitable as primers or hybridization probes for the detection of NMT-encoding nucleic acids (e.g., fragments of at least 15 nucleotides (e.g., at least 18, 20, or 25 nucleotides)).

The invention features a nucleic acid molecule which is at least 65% (or 75%, 85%, 95%, or 98%) identical to the nucleotide sequence shown in SEQ ID NO:1, or SEQ ID NO:3, or the nucleotide sequence of the cDNA insert of the plasmid deposited with ATCC as Accession Number (the "cDNA of ATCC PTA-1663"), or a complement thereof.

The invention features a nucleic acid molecule which includes a fragment of at least 300 (e.g., 325, 350, 375, 400, 425, 450, 500, 550, 600, 650, 700, 800, 900, 1000, 1200, 1400, 1600, or 1770) nucleotides of the nucleotide sequence shown in SEQ ID NO:1, or SEQ ID NO:3, or the nucleotide sequence of the cDNA ATCC PTA-1663, or a complement thereof.

The invention also features a nucleic acid molecule which includes a nucleotide sequence encoding a protein having an amino acid sequence that is at least 65% (or 75%, 85%, 95%, or 98%) identical to the amino acid sequence of SEQ ID NO:2 or the amino acid sequence encoded by the cDNA of ATCC PTA-1663.

Also within the invention is a nucleic acid molecule that encodes a fragment of a polypeptide having the amino acid sequence of SEQ ID NO:2, the fragment including at least 15 (25, 30, 50, 100, 150, 300, 400, or 450) contiguous amino acids of SEQ ID NO:2 or the polypeptide encoded by the cDNA of ATCC Accession Number PTA-1663.

In other embodiments, the invention features an isolated NMT protein having an amino acid sequence that is at least about 65% (e.g., 75%, 85%, 95%, or 98%) identical to the amino acid sequence of SEQ ID NO:2; and an isolated NMT protein which is encoded by a nucleic acid molecule having a nucleotide sequence that is at least about 65% (e.g., 75%, 85%, or 95%) identical to SEQ ID NO:1 or the cDNA of ATCC PTA-1663; and an isolated NMT protein which is encoded by a nucleic acid molecule having a nucleotide sequence which hybridizes under stringent hybridization conditions to a nucleic acid molecule having the nucleotide sequence of SEQ ID NO:1 or the non-coding strand of the cDNA of ATCC PTA-1663.

Another embodiment of the invention features NMT nucleic acid molecules which specifically detect Aspergillus NMT nucleic acid molecules relative to nucleic acid molecules encoding other N-myristoyltransferases. For example, in one embodiment, an Aspergillus NMT nucleic acid molecule hybridizes under stringent conditions to a nucleic acid molecule comprising the nucleotide sequence of SEQ ID NO:1, SEQ ID NO:3, or the cDNA of ATCC PTA-1663, or a complement thereof. In another embodiment, the Aspergillus NMT nucleic acid molecule is at least 300 (e.g., 400, 500, 700, 900, 1100, or 1300) nucleotides in length and hybridizes under stringent conditions to a nucleic acid molecule comprising the nucleotide sequence shown in SEQ ID NO:1, SEQ ID NO:3, the cDNA of ATCC PTA-1663, or a complement thereof. In another embodiment, the invention provides an isolated nucleic acid molecule which is antisense to the coding strand of an Aspergillus NMT nucleic acid.

Another aspect of the invention provides a vector, e.g., a recombinant expression vector, comprising an NMT nucleic acid molecule of the invention. In another embodiment the invention provides a host cell containing such a vector. The invention also provides a method for producing NMT protein by culturing, in a suitable medium, a host cell of the invention containing a recombinant expression vector such that a NMT protein is produced.

Another aspect of this invention features isolated or recombinant NMT proteins and polypeptides. Preferred NMT proteins and polypeptides possess at least one biological activity possessed by naturally occurring Aspergillus NMT, e.g., an ability to catalyze transfer of myristate from myristoyl-CoA to the N-terminal glycine residue of a polypeptide. It is not necessary that the NMT polypeptide have an N-myristoyltransferase activity that is equivalent to that of the wild-type Aspergillus NMT. For example, the NMT polypeptide can have 20, 50, 75, 90, 100, or an even higher percent of the wild-type activity.

Now that the Aspergillus NMT gene, which is essential for survival, has been identified, nucleic acids encoding Aspergillus NMT and Aspergillus NMT proteins can be used to identify antifungal agents. Such antifungal agents can readily be identified with high throughput assays to detect inhibition of NMT activity. This inhibition can be caused by small molecules binding directly to the NMT polypeptide or by binding of small molecules to other essential polypeptides in that pathway.

In an exemplary, but not the only assay, a compound is tested for its ability to inhibit Aspergillus NMT in an assay of NMT activity. NMT activity can be assayed by measuring incorporation of labeled myristate (e.g. [$^3$H]myristate) in culture. The effect of a test compound can be determined by adding the test compound to the culture containing the labeled myristate, then comparing the level of labeled myristate in the culture with the level obtained in control cultures. Now that the *Aspergillus fumigatus* NMT gene has been identified, it can readily be cloned into various host cells (e.g., fungi, *E. coli* or yeast) for carrying out such assays in whole cells). Similarly, conventional in vitro assays of NMT activity can be used with the NMT of the invention.

A suitable NMT activity assay has been described by Stone et al., Genes and Dev. 5:1969–1981 (1991), which is incorporated herein by reference. Briefly, [$^3$H]myristate is added to cell cultures to specifically label myristoylated proteins, which can be separated by SDS-PAGE and visualized by autoradiography. The level of myristoylation can subsequently be quantitated by using conventional methods to measure incorporation of [$^3$H]myristate.

In an alternative assay, a promoter that responds to depletion of the NMT polypeptide by upregulation or downregulation is linked to a reporter gene. To identify a promoter that is up- or down-regulated by the depletion of the NMT polypeptide, the gene encoding Aspergillus NMT is deleted from the genome and replaced with a version of the gene in which the sequence encoding the NMT protein is operably linked to a regulatable promoter. The cells containing this regulatable genetic construct are kept alive by the NMT produced from the genetic construct containing the regulatable promoter. However, the regulatable promoter allows the expression of NMT to be reduced to a level that causes growth inhibition. Total RNA prepared from Aspergillus under such growth-limiting conditions is compared with RNA from wild-type cells. Standard methods of transcriptional profiling can be used to identify mRNA species that are either more or less abundant (i.e., up- or down-regulated) when expressed under the limiting conditions. Genomic sequence information, e.g., from GenBank, can be used to identify the promoter that drives expression of the identified RNA species. Such promoters are up- or down-regulated by depletion of the NMT polypeptide.

Having identified a promoter(s) that is up- or down-regulated by depletion of the NMT polypeptide, the promoter(s) is operably linked to a reporter gene (e.g., β-galactosidase, gus, or GFP). A fungal strain containing this reporter gene construct is then exposed to test compounds. Compounds that inhibit the essential polypeptide (or other polypeptides in the essential pathway in which the NMT polypeptide participates) will cause a functional depletion of the NMT polypeptide and therefore lead to an upregulation or downregulation of expression the reporter gene. Because NMT is essential for the survival of Aspergillus, compounds that inhibit NMT in such an assay are expected to have antifungal activity and can be further tested, if desired, in standard susceptibility assays.

Another suitable method for identifying antifungal compounds involves screening for small molecules that specifically bind to an NMT polypeptide. A variety of suitable binding assays are known in the art as described, for example, in U.S. Pat. Nos. 5,585,277 and 5,679,582, hereby incorporated herein by reference. For example, in various conventional assays, test compounds can be assayed for their ability to bind an NMT polypeptide by measuring the ability of the small molecule to stabilize the NMT polypeptide in its folded, rather than unfolded, state. More specifically, one can measure the degree of protection against unfolding that is afforded by the test compound. Test compounds that bind the NMT polypeptide with high affinity cause, for example, a large shift in the temperature at which the polypeptide is denatured. Test compounds that stabilize the polypeptide in a folded state can be further tested for antifungal activity in a standard susceptibility assay.

In a related method for identifying antifungal compounds, an NMT polypeptide is used to isolate peptide or nucleic acid ligands that specifically bind the NMT polypeptides. These peptide or nucleic acid ligands are then used in a displacement screen to identify small molecules that bind to the NMT polypeptide. Such binding assays can be carried out essentially as described above.

The Aspergillus NMT polypeptides also can be used, in assays to identify test compounds that bind to the polypeptides. Test compounds that bind the NMT polypeptides then can readily be tested, in conventional assays, for their ability to inhibit fungal growth. Test compounds that bind the essential polypeptides are candidate antifungal agents, in contrast to compounds that do not bind the essential polypeptides. As described herein, any of a variety of art-known methods can be used to assay for binding of test compounds to the essential polypeptides.

The invention includes, for example, a method for identifying an antifungal agent where the method entails: (a) contacting an NMT polypeptide with a test compound; (b) detecting binding of the test compound to the polypeptide; and (c) determining whether a test compound that binds to the polypeptide inhibits growth of Aspergillus, relative to growth of fungi cultured in the absence of the test compound that binds to the NMT polypeptide, as an indication that the test compound is an antifungal agent.

In still another method, binding of a test compound to an NMT polypeptide can be detected in a conventional two-hybrid system for detecting protein/protein interactions (e.g., in yeast or mammalian cells). A test compound found to bind the essential polypeptide can be further tested for antifungal activity in a conventional susceptibility assay. Generally, in such two-hybrid methods, (a) the essential polypeptide is provided as a fusion protein that includes the polypeptide fused to (i) a transcription activation domain of a transcription factor or (ii) a DNA-binding domain of a transcription factor; (b) the test polypeptide is provided as a fusion protein that includes the test polypeptide fused to (i) a transcription activation domain of a transcription factor or (ii) a DNA-binding domain of a transcription factor; and (c) binding of the test polypeptide to the polypeptide is detected as a reconstitution of a transcription factor. Reconstitution of the transcription factor can be detected, for example, by detecting transcription of a gene that is operably linked to a DNA sequence bound by the DNA-binding domain of the reconstituted transcription factor (See, for example, White, 1996, Proc. Natl. Acad. Sci. 93:10001–10003 and references cited therein and Vidal et al., 1996, Proc. Natl. Acad. Sci. 93:10315–10320).

In an alternative method, an isolated nucleic acid molecule encoding an NMT is used to identify a compound that decreases the expression of NMT in vivo (i.e., in an Aspergillus cell). Such compounds can be used as antifungal agents. To discover such compounds, cells that express an NMT are cultured, exposed to a test compound (or a mixture of test compounds), and the level of NMT expression or activity is compared with the level of NMT expression or activity in cells that are otherwise identical but that have not been exposed to the test compound(s). Standard quantitative assays of gene expression and NMT activity can be utilized in this aspect of the invention.

To identify compounds that modulate expression of NMT the test compound(s) can be added at varying concentrations to the culture medium of Aspergillus. Such test compounds can include small molecules (typically, non-protein, non-polysaccharide chemical entities), polypeptides, and nucleic acids. The expression of NMT is then measured, for example, by Northern blot PCR analysis or RNAse protection analyses using a nucleic acid molecule of the invention as a probe. The level of expression in the presence of the test molecule, compared with the level of expression in its absence, will indicate whether or not the test molecule alters the expression of the essential polypeptide. Because NMT is essential for survival, test compounds that inhibit the expression and/or function of NMT will inhibit growth of, or kill, the cells that express NMT.

Typically, the test compound will be a small organic molecule. Alternatively, the test compound can be a test polypeptide (e.g., a polypeptide having a random or predetermined amino acid sequence; or a naturally-occurring or synthetic polypeptide) or a nucleic acid, such as a DNA or RNA molecule. The test compound can be a naturally-occurring compound or it can be synthetically produced, if desired. Synthetic libraries, chemical libraries, and the like can be screened to identify compounds that bind NMT. More generally, binding of a test compound to an NMT polypeptide can be detected either in vitro or in vivo. If desired, the above-described methods for identifying compounds that modulate the expression of the NMT polypeptides of the invention can be combined with measuring the levels of NMT expressed in cells, e.g., by carrying out an assay of NMT activity, as described above or, for example, performing a Western blot analysis using antibodies that bind NMT. The antifungal agents identified in the methods of the invention can be used to inhibit a wide spectrum of pathogenic or non-pathogenic fungal strains.

The invention includes pharmaceutical formulations that include a pharmaceutically acceptable excipient and an antifungal agent identified using the methods described herein. In particular, the invention includes pharmaceutical formulations that contain antifungal agents that inhibit the growth of, or kill, pathogenic fungal strains (e.g., pathogenic *Aspergillus fumigatus* strains). Such pharmaceutical formulations can be used in a method of treating a fungal infection in an organism. Such a method entails administering to the organism a therapeutically effective amount of the pharmaceutical formulation, i.e., an amount sufficient to ameliorate signs and/or symptoms of the fungal infection. In particular, such pharmaceutical formulations can be used to treat fungal infections in mammals such as humans and domesticated mammals (e.g., cows, pigs, dogs, and cats), and in plants. The efficacy of such antifungal agents in humans can be estimated in an animal model system well known to those of skill in the art (e.g., mouse systems of fungal infections).

Various affinity reagents that are permeable to the microbial membrane (i.e., antibodies and antibody fragments) are useful in practicing the methods of the invention. For example polyclonal and monoclonal antibodies that specifically bind to the Aspergillus NMT polypeptide can facilitate detection of Aspergillus NMT in various fungal strains (or extracts thereof). These antibodies also are useful for detecting binding of a test compound to NMT (e.g., using the assays described herein). In addition, monoclonal antibodies that specifically bind Aspergillus NMT can themselves be used as antifungal agents.

In another aspect, the invention features a method for detecting an Aspergillus NMT polypeptide in a sample. This method includes: obtaining a sample suspected of containing an Aspergillus NMT polypeptide; contacting the sample with an antibody that specifically binds to an Aspergillus NMT polypeptide under conditions that allow the formation of complexes of an antibody and the NMT polypeptide; and detecting the complexes, if any, as an indication of the presence of an Aspergillus NMT polypeptide in the sample.

The invention offers several advantages. For example, the methods for identifying antifungal agents can be configured for high throughput screening of numerous candidate antifungal agents. Because the NMT gene disclosed herein is thought to be highly conserved, antifungal drugs targeted to this gene or its gene products are expected to have a broad spectrum of antifungal activity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated herein by reference in their entirety. In the case of a conflict, the present specification, including definitions, will control. In addition, the materials, methods, and examples are illustrative and are not intended to limit the scope of the invention, which is defined by the claims.

Other features and advantages of the invention will be apparent from the following detailed description, and from the claims.

BRIEF DESCRIPTION OF THE DRAWINGS

FIGS. 1A and 1B are a listing of the nucleotide sequence (SEQ ID NO:1) and predicted amino acid sequence (SEQ ID NO:2) of *Aspergillus fumigatus* N-myristoyl transferase (NMT).

FIGS. 2A, 2B and 2C are a listing of the genomic (SEQ ID NO:3) and predicted amino acid sequences (SEQ ID NO:2) of *Aspergillus fumigatus* NMT.

DETAILED DESCRIPTION OF THE INVENTION

A gene encoding N-myristoyltransferase of *Aspergillus fumigatus* has been identified and is essential for the survival of Aspergillus. The NMT gene and polypeptide are useful targets for identifying compounds that are inhibitors of the fungi in which NMT polypeptides are expressed.

Nucleic acids include both RNA and DNA, including genomic DNA and synthetic (e.g., chemically synthesized) DNA. Nucleic acids can be double-stranded or single-stranded. Where single-stranded, the nucleic acid may be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An isolated nucleic acid is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence. The term "isolated" refers to a nucleic acid or polypeptide that is substantially free of cellular material, viral material, or culture medium (when produced by recombinant DNA techniques), or chemical precursors or other chemicals (when chemically synthesized). Moreover, an isolated nucleic acid fragment is a nucleic acid fragment that is not naturally occurring as a fragment and would not be found in the natural state.

Figure 2B:
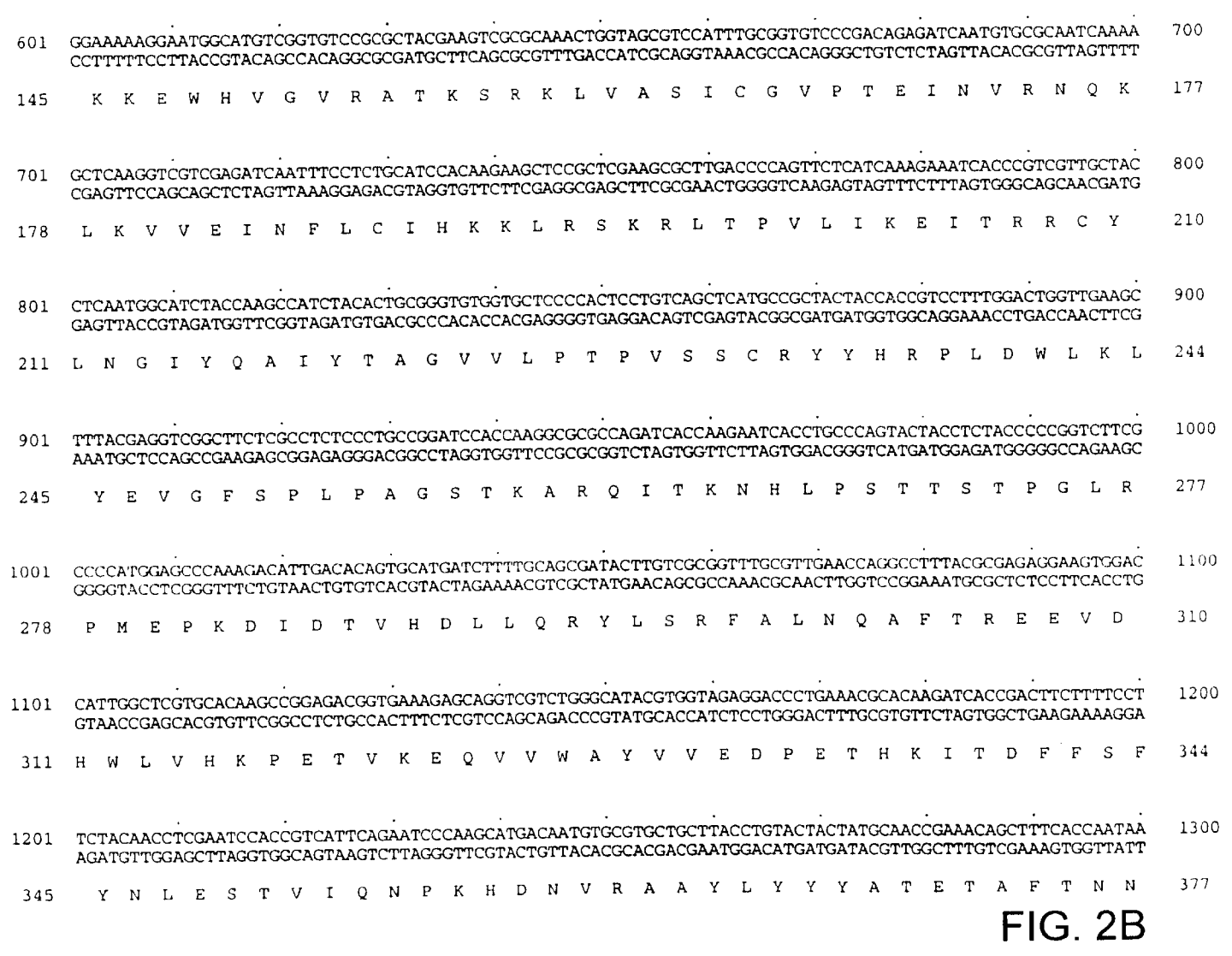

A nucleic acid sequence that is substantially identical to an essential nucleotide sequence is at least 80% identical to the nucleotide sequence of NMT as represented by the SEQ ID NOs:1 and 3, as depicted in FIGS. 1A–1B and 2A–2C. For purposes of comparison of nucleic acids, the length of the reference nucleic acid sequence will generally be at least 40 nucleotides, e.g., at least 60 nucleotides or more nucleotides.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of overlapping positions×100). Preferably, the two sequences are the same length.

The determination of percent homology between two sequences can be accomplished using a mathematical algorithm. A preferred, non-limiting example of a mathematical algorithm utilized for the comparison of two sequences is the algorithm of Karlin and Altschul (1990) *Proc. Nat'l Acad. Sci. USA* 87:2264–2268, modified as in Karlin and Altschul (1993) *Proc. Nat'l Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to NMT nucleic acid molecules of the invention. BLAST protein searches can be performed with the XBLAST program, score=50, wordlength=3 to obtain amino acid sequences homologous to NMT protein molecules of the invention. To obtain gapped alignments for comparison purposes, Gapped BLAST can be utilized as described in Altschul et al., (1997) *Nucleic Acids Res*. 25:3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The NMT polypeptides of the invention include, but are not limited to, recombinant polypeptides and natural polypeptides. Also included are nucleic acid sequences that encode forms of NMT polypeptides in which naturally occurring amino acid sequences are altered or deleted. Preferred nucleic acids encode polypeptides that are soluble under normal physiological conditions. Also within the invention are nucleic acids encoding fusion proteins in which a portion of the NMT polypeptide is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells. The invention also includes, for example, isolated polypeptides (and the nucleic acids that encode these polypeptides) that include a first portion and a second portion; the first portion includes, e.g., an NMT polypeptide, and the second portion includes an immunoglobulin constant (Fc) region or a detectable marker.

The fusion partner can be, for example, a polypeptide which facilitates secretion, e.g., a secretory sequence. Such a fused polypeptide is typically referred to as a preprotein. The secretory sequence can be cleaved by the host cell to form the mature protein. Also within the invention are nucleic acids that encode an essential polypeptide fused to a polypeptide sequence to produce an inactive preprotein. Preproteins can be converted into the active form of the protein by removal of the inactivating sequence.

The invention also includes nucleic acids that hybridize, e.g., under stringent hybridization conditions (as defined herein) to all or a portion of the nucleotide sequences represented by SEQ ID NO:1 or 3, or their complements. The hybridizing portion of the hybridizing nucleic acids is typically at least 15 (e.g., 20, 30, or 50) nucleotides in length. The hybridizing portion of the hybridizing nucleic acid is at least 60%, e.g., at least 70%, 80%, 95%, or at least 98%, identical to the sequence of a portion or all of a nucleic acid encoding an NMT polypeptide or its complement. Hybridizing nucleic acids of the type described herein can be used as a cloning probe, a primer (e.g., a PCR primer), or a diagnostic probe. Nucleic acids that hybridize to the nucleotide sequences represented by SEQ ID NOs: 1 and 3 are considered "antisense oligonucleotides."

Also useful in the invention are various engineered cells, e.g., transformed host cells, that contain an NMT nucleic acid described herein. A transformed cell is a cell into which (or into an ancestor of which) has been introduced, by means of recombinant DNA techniques, a nucleic acid encoding an essential polypeptide. Both prokaryotic and eukaryotic cells are included, e.g., fungi, and bacteria, such as *E. coli*, and the like.

Also useful in the invention are genetic constructs (e.g., vectors and plasmids) that include a nucleic acid of the invention which is operably linked to a transcription and/or translation sequence to enable expression, e.g., expression vectors. A selected nucleic acid, e.g., a DNA molecule encoding an NMT polypeptide, is "operably linked" when it is positioned adjacent to one or more sequence elements, e.g., a promoter, which direct transcription and/or translation of the sequence such that the sequence elements can control transcription and/or translation of the selected nucleic acid.

The invention also features purified or isolated polypeptides encoded by the Aspergillus NMT coding sequence. The terms "protein" and "polypeptide" both refer to any chain of amino acids, regardless of length or post-translational modification (e.g., glycosylation or phosphorylation). Thus, the term NMT polypeptide includes full-length, naturally occurring, isolated NMT proteins, as well as recombinantly or synthetically produced polypeptides that correspond to the full-length, naturally occurring proteins, or to a portion of the naturally occurring or synthetic polypeptide.

A purified or isolated compound is a composition that is at least 60% by weight the compound of interest, e.g., an NMT polypeptide or antibody. Preferably the preparation is at least 75% (e.g., at least 90%, 95%, or even 99%) by weight the compound of interest. Purity can be measured by any appropriate standard method, e.g., column chromatography, polyacrylamide gel electrophoresis, or HPLC analysis.

Preferred NMT polypeptides include a sequence substantially identical to all or a portion of a naturally occurring Aspergillus NMT polypeptide, e.g., including all or a portion of the sequences shown in FIGS. 2A–2C. Polypeptides "substantially identical" to the NMT polypeptide sequences described herein have an amino acid sequence that is at least 65% identical to the amino acid sequence of the NMT polypeptide represented by the SEQ ID NO:2 (measured as described herein). The new polypeptides can also have a greater percentage identity, e.g., 85%, 90%, 95%, or even higher. For purposes of comparison, the length of the reference NMT polypeptide sequence will generally be at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. It also might be a 100 amino acid long polypeptide which is 50% identical to the reference polypeptide over its entire length. Of course, other polypeptides also will meet the same criteria.

The invention also features purified or isolated antibodies that specifically bind to an Aspergillus NMT polypeptide. An antibody "specifically binds" to a particular antigen, e.g., an NMT polypeptide, when it binds to that antigen, but does not substantially recognize and bind to other molecules in a sample, e.g., a biological sample, that naturally includes an NMT polypeptide. In addition, an antibody specifically binds to an Aspergillus NMT polypeptide when it does not substantially bind to NMT polypeptides from other genuses (e.g., Saccharomyces, Candida), particularly NMT polypeptides of an organism to be treated by the methods of the invention (e.g., humans, or domesticated animals).

Identifying the *Aspergillus Fumigatus* NMT Gene

As shown by the experiments described below, the *Aspergillus fumigatus* NMT gene is essential for survival. *Aspergillus fumigatus* is available from the ATCC. The Aspergillus NMT gene was cloned using polymerase chain reaction technology and degenerate primers based on the *Saccharomyces cerevisiae* and *Candida albicans* NMT genes. The degenerate primer termed degNMT-2 had the sequence: 5'RAN MAY TAY GTN GAR GA3' (SEQ ID NO:4) and the primer degNMT-4G had the sequence 5'CAN ARR AAR TTD ATY TCN AC3' (SEQ ID NO:5), where "R" represents adenine or guanine; "N" represents adenine, guanine, cytosine, or thymine; "Y" represents cytosine or thymine; and "D" represents adenine, thymine, or guanine. These degenerate primers were used to amplify genomic *Aspergillus fumigatus* DNA using 35 cycles of: 94° C. for 1 minute, 40° C. for 2 minutes, and 72° C. for 3 minutes. The resulting PCR product was subcloned into the pBluescript cloning vector (Stratagene; La Jolla, Calif.), then sequenced. Based on the resulting sequence, two exact-match primers were created: primer AfNMT-5 has the sequence 5'TGC CAT CTT CCG GTT CAG A3' (SEQ ID NO:6), and the primer AfNMT-7 has the sequence 5'TGC GCG ACT TCG TAG CGC GGA3' (SEQ ID NO:7). These primers were used to PCR amplify the 5' and 3' halves of the AfNMT from an *Aspergillus fumigatus* cDNA library. The cDNA library was made using the vector pYES2 (Invitrogen; Palo Alto, Calif.). For PCR amplification, the AfNMT-5 primer was paired with a primer hybridizing to the 3' sequence of the multiple cloning site of pYES2. The AfNMT-7 primer was paired with a primer hybridizing to the pGAL sequences in pYES2. PCR amplification of the 5' and 3' halves of the NMT gene was carried out with 30 cycles of 94° C. for 30 seconds, 55° C. for 30 seconds, 720 for and 2.5 minutes. The resulting PCR products were cloned into the pBluescript vector and sequenced to obtain the CDNA sequence of *Aspergillus fumigatus* NMT. The entire NMT open reading frame was subsequently amplified using primers that exactly matched each of (a) the first methionine codon and (b) the stop codon of the NMT open reading frame. These primers were: AfNMT-N 5'CGC GCA TAT GGC GGA GTC GCT ATT GGA AAA CAA CCC CGC3' (SEQ ID NO:8) for the methionine codon and AfNMT-C: 5'GCA GCG GCC GCT TAC AGC ATA ACG ATG CCA ACG CCT GCC3' (SEQ ID NO:9) for the stop codon. The amplified open reading frame subsequently was cloned into the pCRTOPO vector (Invitrogen) using TA cloning methods (Invitrogen).

Identification of NMT Genes in Additional Fungal Strains

Now that the *Aspergillus fumigatus* NMT gene has been identified, this gene, or fragments thereof, can be used to detect homologous genes in yet other organisms. Fragments of a nucleic acid (DNA or RNA) encoding an NMT polypeptide (or sequences complementary thereto) can be used as probes in conventional nucleic acid hybridization assays of various organism. For example, nucleic acid probes (which typically are 8–30, or usually 15–20, nucleotides in length) can be used to detect NMT genes in art-known molecular biology methods, such as Southern blotting, Northern blotting, dot or slot blotting, PCR amplification methods, colony hybridization methods, and the like. Typically, an oligonucleotide probe based on the nucleic acid sequences described herein, or fragment thereof, is labeled and used to screen a genomic library constructed from mRNA obtained from a fungal strain of interest. A suitable method of labeling involves using polynucleotide kinase to add $^{32}$P-labeled ATP to the oligonucleotide used as the probe. This method is well known in the art, as are several other suitable methods (e.g., biotinylation and enzyme labeling).

Hybridization of the oligonucleotide probe to the library, or other nucleic acid sample, typically is performed under moderate to high stringency conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming that 1% mismatching results in a 1° C. decrease in the $T_m$, the temperature of the final wash in the hybridization reaction is reduced accordingly (for example, if sequences having ≧95% identity with the probe are sought, the final wash temperature is decreased by 5° C.). In practice, the change in $T_m$ can be between 0.5° and 1.5° C. per 1% mismatch.

High stringency conditions include, for example, hybridizing at 68° C. in 5×SSC/5×Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In one approach, libraries constructed from pathogenic or non-pathogenic fungal strains can be screened. For example, such strains can be screened for expression of the NMT gene of the invention by Northern blot analysis. Upon detection of transcripts of the essential genes thereof, libraries can be constructed from RNA isolated from the appropriate strain, utilizing standard techniques well known to those of skill in the art. Alternatively, a total genomic DNA library can be screened using an NMT gene probe.

New gene sequences can be isolated, for example, by performing PCR using two degenerate oligonucleotide primer pools designed on the basis of nucleotide sequences within the NMT gene as depicted herein. The template for the reaction can be DNA obtained from strains known or suspected to express the NMT gene of the invention. The PCR product can be subcloned and sequenced.

Synthesis of the various NMT polypeptides (or an antigenic fragment thereof) for use as antigens, or for other purposes, can readily be accomplished using any of the various art-known techniques. For example, an NMT polypeptide, or an antigenic fragment(s), can be synthesized chemically in vitro, or enzymatically (e.g., by in vitro transcription and translation). Alternatively, the gene can be expressed in, and the polypeptide purified from, a cell (e.g., a cultured cell) by using any of the numerous, available gene expression systems. For example, the polypeptide antigen can be produced in a prokaryotic host (e.g., *E. coli*) or in eukaryotic cells, such as yeast cells.

Proteins and polypeptides can also be produced in plant cells, if desired. For plant cells, viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The optimal methods of transformation or transfection and the choice of expression vehicle will depend on the host system selected. Transformation and transfection methods are described, e.g., in Ausubel et al., supra; expression vehicles may be chosen from those provided, e.g., in *Cloning Vectors*: A Laboratory Manual (P. H. Pouwels et al., 1985, Supp. 1987). The host cells harboring the expression vehicle can be cultured in conventional nutrient media, adapted as needed for activation of a chosen gene, repression of a chosen gene, selection of transformants, or amplification of a chosen gene.

If desired, NMT polypeptide can be produced as a fusion protein. For example, the expression vector pUR278 (Ruther et al., *EMBO J.*, 2:1791, 1983) can be used to create lacZ fusion proteins. The art-known pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an exemplary expression system, a baculovirus such as *Autographa californica* nuclear polyhedrosis virus (AcNPV), which grows in *Spodoptera frugiperda* cells, can be used as a vector to express foreign genes. A coding sequence encoding an essential polypeptide can be cloned into a non-essential region (for example the polyhedrin gene) of the viral genome and placed under control of a promoter, e.g., the polyhedrin promoter or an exogenous promoter. Successful insertion of a gene encoding an essential polypeptide can result in inactivation of the polyhedrin gene and production of non-occluded recombinant virus (i.e., virus lacking the proteinaceous coat encoded by the polyhedrin gene). These recombinant viruses are then typically used to infect insect cells (e.g., *Spodoptera frugiperda* cells) in which the inserted gene is expressed (see, e.g., Smith et al., *J. Virol.*, 46:584, 1983; Smith, U.S. Pat. No. 4,215,051). If desired, mammalian cells can be used in lieu of insect cells, provided that the virus is engineered such that the gene encoding the NMT polypeptide is placed under the control of a promoter that is active in mammalian cells.

In mammalian host cells, a number of viral-based expression systems can be utilized. When an adenovirus is used as an expression vector, the nucleic acid sequence encoding the NMT polypeptide can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing an NMT gene product in infected hosts (see, e.g., Logan, Proc. Natl. Acad. Sci. USA, 81:3655, 1984).

Specific initiation signals may be required for efficient translation of inserted nucleic acid sequences. These signals include the ATG initiation codon and adjacent sequences. In general, exogenous translational control signals, including, perhaps, the ATG initiation codon, should be provided. Furthermore, the initiation codon must be in phase with the reading frame of the desired coding sequence to ensure translation of the entire sequence. These exogenous translational control signals and initiation codons can be of a variety of origins, both natural and synthetic. The efficiency of expression may be enhanced by the inclusion of appropriate transcription enhancer elements, or transcription terminators (Bittner et al., *Methods in Enzymnol.*, 153:516, 1987).

The NMT polypeptide can be expressed individually or as a fusion with a heterologous polypeptide, such as a signal sequence or other polypeptide having a specific cleavage site at the N-and/or C-terminus of the protein or polypeptide. The heterologous signal sequence selected should be one that is recognized and processed, i.e., cleaved by a signal peptidase, by the host cell in which the fusion protein is expressed.

A host cell can be chosen that modulates the expression of the inserted sequences, or modifies and processes the gene product in a specific, desired fashion. Such modifications and processing (e.g., cleavage) of protein products may facilitate optimal functioning of the protein. Various host cells have characteristic and specific mechanisms for post-translational processing and modification of proteins and gene products. Appropriate cell lines or host systems familiar to those of skill in the art of molecular biology can be chosen to ensure the correct modification and processing of the foreign protein expressed. To this end, eukaryotic host cells that possess the cellular machinery for proper processing of the primary transcript, and phosphorylation of the gene product can be used. Such mammalian host cells include, but are not limited to, CHO, VERO, BHK, HeLa, COS, MDCK, 293, 3T3, WI38, and choroid plexus cell lines.

If desired, the NMT polypeptide can be produced by a stably-transfected mammalian cell line. A number of vectors suitable for stable transection of mammalian cells are available to the public, see, e.g., Pouwels et al. (supra); methods for constructing such cell lines are also publicly known, e.g., in Ausubel et al. (supra). In one example, DNA encoding the protein is cloned into an expression vector that includes the dihydrofolate reductase (DHFR) gene. Integration of the plasmid and, therefore, the essential polypeptide-encoding gene into the host cell chromosome is selected for by including 0.01–300 $\mu$M methotrexate in the cell culture medium (as described in Ausubel et al., surra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra).

A number of other selection systems can be used, including but not limited to, herpes simplex virus thymidine kinase genes, hypoxanthine-guanine phosphoribosyltransferase genes, and adenine phosphoribosyltransferase genes, which can be employed in tk, hgprt, or aprt cells, respectively. In addition, gpt, which confers resistance to mycophenolic acid (Mulligan et al., *Proc. Natl. Acad. Sci. USA*, 78:2072, 1981); neo, which confers resistance to the aminoglycoside G-418 (Colberre-Garapin et al., *J. Mol. Biol.*, 150:1, 1981); and hygro, which confers resistance to hygromycin (Santerre et al., *Gene*, 30:147, 1981), can be used.

Alternatively, any fusion protein can be readily purified by utilizing an antibody or other molecule that specifically binds the fusion protein being expressed. For example, a system described in Janknecht et al., *Proc. Natl. Acad. Sci. USA*, 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, an NMT polypeptide, or a portion thereof, can be fused to an immunoglobulin Fc domain. Such a fusion protein can be readily purified using a protein A column, for example. Moreover, such fusion proteins permit the production of a chimeric form of an NMT polypeptide having increased stability in vivo.

Once the recombinant NMT polypeptide is expressed, it can be isolated (i.e., purified). Secreted forms of the polypeptides can be isolated from cell culture media, while non-secreted forms must be isolated from the host cells. Polypeptides can be isolated by affinity chromatography. For example, an anti-NMT antibody (e.g., produced as described herein) can be attached to a column and used to isolate the protein. Lysis and fractionation of cells harboring the protein prior to affinity chromatography can be performed by standard methods (see, e.g., Ausubel et al., supra). Alternatively, a fusion protein can be constructed and used to isolate an NMT polypeptide (e.g., a NMT-maltose binding fusion protein, a NMT-$\beta$-galactosidase fusion protein, or a NMT-trpE fusion protein; see, e.g., Ausubel et al., supra; New England Biolabs Catalog, Beverly, Mass.). The recombinant protein can, if desired, be further purified, e.g., by high performance liquid chromatography using standard techniques (see, e.g., Fisher, *Laboratory Techniques In Biochemistry And Molecular Biology*, eds., Work and Burdon, Elsevier, 1980).

Given the amino acid sequences described herein, polypeptides useful in practicing the invention, particularly fragments of essential polypeptides, can be produced by standard chemical synthesis (e.g., by the methods described in *Solid Phase Peptide Synthesis*, 2nd ed., The Pierce Chemical Co., Rockford, Ill., 1984) and used as antigens, for example.

Antibodies

The NMT polypeptides (or antigenic fragments or analogs of such polypeptides) can be used to raise antibodies useful in the invention, and such polypeptides can be produced by recombinant or peptide synthetic techniques (see, e.g., *Solid Phase Peptide Synthesis*, supra; Ausubel et al., supra). In general, the polypeptides can be coupled to a carrier protein, such as KLH, as described in Ausubel et al., supra, mixed with an adjuvant, and injected into a host mammal. A "carrier" is a substance that confers stability on, and/or aids or enhances the transport or immunogenicity of, an associated molecule. Antibodies can be purified, for example, by affinity chromatography methods in which the polypeptide antigen is immobilized on a resin.

In particular, various host animals can be immunized by injection of a polypeptide of interest. Examples of suitable host animals include rabbits, mice, guinea pigs, and rats. Various adjuvants can be used to increase the immunological response, depending on the host species, including but not limited to Freund's (complete and incomplete adjuvant), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum*. Polyclonal antibodies are heterogeneous populations of antibody molecules derived from the sera of the immunized animals.

Antibodies useful in the invention include monoclonal antibodies, polyclonal antibodies, humanized or chimeric antibodies, single chain antibodies, Fab fragments, F(ab')$_2$ fragments, and molecules produced using a Fab expression library.

Monoclonal antibodies (mAbs), which are homogeneous populations of antibodies to a particular antigen, can be prepared using NMT, and standard hybridoma technology (see, e.g., Kohler et al., *Nature*, 256:495, 1975; Kohler et al., *Eur. J. Immunol.*, 6:511, 1976; Kohler et al., *Eur. J. Immunol.*, 6:292, 1976; Hammerling et al., In *Monoclonal Antibodies and T Cell Hybridomas*, Elsevier, N.Y., 1981; Ausubel et al., supra).

In particular, monoclonal antibodies can be obtained by any technique that provides for the production of antibody molecules by continuous cell lines in culture, such as those described in Kohler et al., *Nature*, 256:495, 1975, and U.S. Pat. No. 4,376,110; the human B-cell hybridoma technique (Kosbor et al., *Immunology Today*, 4:72, 1983; Cole et al., *Proc. Natl. Acad. Sci. USA*, 80:2026, 1983); and the EBV-hybridoma technique (Cole et al., *Monoclonal Antibodies and Cancer Therapy*, Alan R. Liss, Inc., pp. 77–96, 1983). Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies are tested for specific recognition of Aspergillus NMT in an immunoassay, such as a Western blot or immunoprecipitation analysis using standard techniques, e.g., as described in Ausubel et al., supra. Antibodies that specifically bind to the NMT polypeptide, or conservative variants are useful in the invention. For example, such antibodies can be used in an immunoassay to detect an NMT polypeptide in pathogenic or non-pathogenic strains of fungi.

Preferably, antibodies of the invention are produced using fragments of NMT that appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

If desired, several (e.g., two or three) fusions can be generated for each protein, and each fusion can be injected into at least two rabbits. Antisera can be raised by injections in a series, typically including at least three booster injections. Typically, the antisera is checked for its ability to immunoprecipitate a recombinant essential polypeptide, or unrelated control proteins, such as glucocorticoid receptor, chloramphenicol acetyltransferase, or luciferase.

Techniques developed for the production of "chimeric antibodies" (Morrison et al., *Proc. Natl. Acad. Sci.*, 81:6851, 1984; Neuberger et al., *Nature*, 312:604, 1984Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; and U.S. Pat. Nos. 4,946,778 and 4,704,692) can be adapted to produce single chain antibodies against an NMT polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to F(ab')$_2$ fragments, which can be produced by pepsin digestion of the antibody molecule, and Fab fragments, which can be generated by reducing the disulfide bridges of F(ab')$_2$ fragments. Alternatively, Fab expression libraries can be constructed (Huse et al., *Science*, 246:1275, 1989) to allow rapid and easy identification of monoclonal Fab fragments with the desired specificity.

Polyclonal and monoclonal antibodies that specifically bind to an NMT polypeptide can be used, for example, to detect expression of NMT in another strain of fungi. For example, an NMT polypeptide can be readily detected in conventional immunoassays of fungal cells or extracts. Examples of suitable assays include, without limitation, Western blotting, ELISAs, radioimmune assays, and the like.

Assay for Antifungal Agents

The invention provides a method for identifying an antifungal agent(s). Although the inventor is not bound by any particular theory as to the biological mechanism involved, the new antifungal agents are thought to inhibit specifically (1) the function of the NMT polypeptide or (2) expression of the NMT gene. In preferred methods, screening for antifungal agents is accomplished by identifying those compounds (e.g., small organic molecules) that inhibit the activity of an NMT polypeptide or the expression of an essential gene.

In an exemplary assay, but not the only assay, a promoter that responds to depletion of the essential polypeptide by upregulation or downregulation is linked to a reporter gene (e.g., β-galactosidase, gus, or GFP), as described above. A fungal strain containing this reporter gene construct is then exposed to test compounds. Compounds that inhibit the NMT (or other polypeptides in the pathway in which NMT participates) will cause a functional depletion of the NMT and therefore lead to an upregulation or downregulation of expression the reporter gene. Because NMT is essential for the survival of Aspergillus, compounds that inhibit the NMT in such an assay are expected to be antifungal agents and can be further tested, if desired, in conventional susceptibility assays.

In other suitable methods, screening for antifungal agents is accomplished by (i) identifying those compounds that bind NMT and (ii) further testing such compounds for their ability to inhibit fungal growth in vitro or in vivo.

Specific binding of a test compound to a polypeptide can be detected, for example, in vitro by reversibly or irreversibly immobilizing the test compound(s) on a substrate, e.g., the surface of a well of a 96-well polystyrene microtitre plate. Methods for immobilizing polypeptides and other small molecules are well known in the art. For example, the microtitre plates can be coated with an NMT polypeptide by adding the polypeptide in a solution (typically, at a concentration of 0.05 to 1 mg/ml in a volume of 1–100 μl) to each well, and incubating the plates at room temperature to 37° C. for 0.1 to 36 hours. Polypeptides that are not bound to the plate can be removed by shaking the excess solution from the plate, and then washing the plate (once or repeatedly) with water or a buffer. Typically, the polypeptide is in water or a buffer. The plate is then washed with a buffer that lacks the bound polypeptide. To block the free protein-binding sites on the plates, the plates are blocked with a protein that is unrelated to the bound polypeptide. For example, 300 µl of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate.

Binding of the test compound to NMT can be detected by any of a variety of art-known methods. For example, an antibody that specifically binds an NMT polypeptide can be used in an immunoassay. If desired, the antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds the Fc portion of an anti-YphC antibody). In an alternative detection method, the NMT polypeptide is labeled, and the label is detected (e.g., by labeling an essential polypeptide with a radioisotope, fluorophore, chromophore, or the like). In still another method, the NMT polypeptide is produced as a fusion protein with a protein that can be detected optically, e.g., green fluorescent protein (which can be detected under UV light). In an alternative method, the polypeptide can be produced as a fusion protein with an enzyme having a detectable enzymatic activity, such as horse radish peroxidase, alkaline phosphatase, β-galactosidase, or glucose oxidase. Genes encoding all of these enzymes have been cloned and are readily available for use by those of skill in the art. If desired, the fusion protein can include an antigen, and such an antigen can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins).

In various in vivo methods for identifying polypeptides that bind NMT, the conventional two-hybrid assays of protein/protein interactions can be used (see e.g., Chien et al., *Proc. Natl. Acad. Sci. USA*, 88:9578, 1991; Fields et al., U.S. Pat. No. 5,283,173; Fields and Song, *Nature*, 340:245, 1989; Le Douarin et al., *Nucleic Acids Research*, 23:876, 1995; Vidal et al., *Proc. Natl. Acad. Sci. USA*, 93:10315–10320, 1996; and White, *Proc. Natl. Acad. Sci. USA*, 93:10001–10003, 1996). Generally, the two-hybrid methods involve in vivo reconstitution of two separable domains of a transcription factor. One fusion protein contains the NMT polypeptide fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the NMT polypeptide to the test polypeptide (i.e., candidate antifungal agent) reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

The methods described above can be used for high throughput screening of numerous test compounds to identify candidate antifungal (or anti-fungal) agents. Having identified a test compound as a candidate antifungal agent, the candidate antifungal agent can be further tested for inhibition of fungal growth in vitro or in vivo (e.g., using an animal, e.g., rodent, model system) if desired. Using other, art-known variations of such methods, one can test the ability of a nucleic acid (e.g., DNA or RNA) used as the test compound to bind NMT.

In vitro, further testing can be accomplished by means known to those in the art such as an enzyme inhibition assay or a whole-cell fungal growth inhibition assay. For example, an agar dilution assay identifies a substance that inhibits fungal growth. Microtiter plates are prepared with serial dilutions of the test compound, adding to the preparation a given amount of growth substrate, and providing a preparation of fungi. Inhibition of fungal growth is determined, for example, by observing changes in optical densities of the fungal cultures.

Inhibition of fungal growth is demonstrated, for example, by comparing (in the presence and absence of a test compound) the rate of growth or the absolute growth of fungal cells. Inhibition includes a reduction of one of the above measurements by at least 20%. Particularly potent test compounds may further reduce the growth rate (e.g., by at least 25%, 30%, 40%, 50%, 75%, 80%, or 90%).

Animal (e.g., rodent such as murine) models of fungal infections are known to those of skill in the art, and such animal model systems are accepted for screening antifungal agents as an indication of their therapeutic efficacy in human patients. In a typical in vivo assay, an animal is infected with a pathogenic strain of fungi, e.g., by inhalation of fungi, and conventional methods and criteria are used to diagnose the mammal as being afflicted with a fungal infection. The candidate antifungal agent then is administered to the mammal at a dosage of 1–100 mg/kg of body weight, and the mammal is monitored for signs of amelioration of disease. Alternatively, the test compound can be administered to the mammal prior to infecting the mammal with the fungi, and the ability of the treated mammal to resist infection is measured. Of course, the results obtained in the presence of the test compound should be compared with results in control animals, which are not treated with the test compound. Administration of candidate antifungal agents to the mammal can be carried out as described below, for example.

Pharmaceutical Formulations

Treatment includes administering a pharmaceutically effective amount of a composition containing an antifungal agent to a subject in need of such treatment, thereby inhibiting fungal growth in the subject. Such a composition typically contains from about 0.1 to 90% by weight (such as 1 to 20% or 1 to 10%) of an antifungal agent of the invention in a pharmaceutically acceptable carrier.

Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method, whereby a pharmaceutical formulation containing the antifungal agent and a physiologically acceptable excipient is infused. Physiologically acceptable excipients may include, for example, 5% dextrose, 0.9% saline, Ringer's solution or other suitable excipients. Intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid, (e.g., ethyl oleate).

A topical semi-solid ointment formulation typically contains a concentration of the active ingredient from about 1 to 20%, e.g., 5 to 10% in a carrier such as a pharmaceutical cream base. Various formulations for topical use include drops, tinctures, lotions, creams, solutions, and ointments containing the active ingredient and various supports and vehicles.

The optimal percentage of the antifungal agent in each pharmaceutical formulation varies according to the formulation itself and the therapeutic effect desired in the specific pathologies and correlated therapeutic regimens. Appropriate dosages of the antifungal agents can be readily determined by those of ordinary skill in the art of medicine by monitoring the mammal for signs of disease amelioration or inhibition, and increasing or decreasing the dosage and/or frequency of treatment as desired. The optimal amount of the antifungal compound used for treatment of conditions caused by or contributed to by fungal infection may depend upon the manner of administration, the age and the body weight of the subject, and the condition of the subject to be treated. Generally, the antifungal compound is administered at a dosage of 1 to 100 mg/kg of body weight, and typically at a dosage of 1 to 10 mg/kg of body weight.

Other Embodiments

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, other art-known assays to detect interactions of test compounds with proteins, or to detect inhibition of fungal growth also can be used with the NMT gene. The invention also includes methods of making a pharmaceutical composition for use in inhibiting Aspergillus. Specifically, the method includes formulating a pharmaceutically acceptable excipient with an antifungal agent, such as those described herein

What is claimed is:

1. An isolated nucleic acid molecule encoding an NMT polypeptide comprising the amino acid sequence of SEQ ID NO:2, as depicted in FIGS. 1A–1B.

2. An isolated nucleic acid molecule comprising a nucleic acid sequence selected from the group consisting of:
   (1) the sequence of SEQ ID NO:1, as depicted in FIGS. 1A–1B, or degenerate variants thereof;
   (2) the sequence of SEQ ID NO:1, or degenerate variants thereof, wherein T is replaced by U;
   (3) nucleic acid sequences complementary to sequences of (1) and (2);
   (4) nucleic acid fragments of sequences of (1), (2), and (3) that are from 18 to 90 base pairs in length and that specifically hybridize at 68° C. in 5×SSC/5×Denhardt's solution/1.0% SDS to genomic DNA encoding the polypeptide of SEQ ID NO:2;
   (5) the sequence of SEQ ID NO:3, as depicted in FIGS. 2A–2C, or degenerate variants thereof;
   (6) the sequence of SEQ ID NO:3, or degenerate variants thereof, wherein T is replaced by U;
   (7) nucleic acid sequences complementary to sequences of (5) and (6); and
   (8) nucleic acid fragments of sequences of (5), (6), and (7) that are from 18 to 90 base pairs in length and that specifically hybridize at 68° C. in 5×SSC/5×Denhardt's solution/1.0% SDS to genomic DNA encoding the polypeptide of SEQ ID NO:2.

3. An isolated nucleic acid molecule from Aspergillus that is at least 95% identical to SEQ ID NO:1 or SEQ ID NO:3 and encodes a fully functional N-myristoyl transferase.

4. An isolated nucleic acid molecule which specifically hybridizes at 68° C. in 5×SSC/5×Denhardt's solution/1.0% SDS to SEQ ID NO: 1 or SEQ ID NO: 3, and encodes a fully functional N-myristoyl transferase.

5. A vector comprising a nucleic acid molecule of claim 1.

6. A vector comprising a nucleic acid molecule of claim 2.

7. An expression vector comprising a nucleic acid molecule of claim 1 operably linked to a nucleotide sequence regulatory element that controls expression of said nucleic acid molecule.

8. An expression vector comprising a nucleic acid molecule of claim 2, wherein said nucleic acid molecule is operably linked to a nucleotide sequence regulatory element that controls expression of said nucleic acid molecule.

9. A host cell comprising an exogenously introduced nucleic acid molecule of claim 1.

10. A host cell comprising an exogenously introduced nucleic acid molecule of claim 2.

11. A host cell of claim 9, wherein the cell is a fungus, yeast, or bacterium.

12. A host cell of claim 10, wherein the cell is a fungus, yeast, or bacterium.

13. A genetically engineered host cell comprising a nucleic acid molecule of claim 1 operably linked to a heterologous nucleotide sequence regulatory element that controls expression of the nucleic acid molecule in the host cell.

14. A host cell of claim 13, wherein the cell is a fungus, yeast or bacterium.

15. A genetically engineered host cell comprising a nucleic acid molecule of claim 2 operably linked to a nucleotide sequence regulatory element that controls expression of the nucleic acid in the host cell.

16. A host cell of claim 15, wherein the cell is a fungus, yeast or bacterium.

17. A method for identifying an antifungal agent, the method comprising:
   (a) contacting a nucleic acid encoding Aspergillus NMT with a test compound; and
   (b) detecting binding of the test compound to the nucleic acid, wherein binding indicates that the test compound is an antifungal agent.

18. A method of claim 17, further comprising:
   (c) determining whether a test compound that binds to the nucleic acid inhibits growth of fungi, relative to growth of fungi cultured in the absence of the test compound that binds the nucleic acid, wherein inhibition of growth indicates that the test compound is an antifungal agent.

19. A method of claim 17, wherein the test compound is selected from the group consisting of polypeptides, small molecules, ribonucleic acids, and deoxyribonucleic acids.

20. An isolated nucleic acid molecule, said molecule comprising the cDNA sequence contained within an American Type Culture Collection (ATCC) accession number PTA-1663.

21. An isolated nucleic acid molecule that comprises from 20 to 90 base pairs and specifically hybridizes at 68° C. in 5×SSC/5× Denhardt's solution/1.0% SDS to SEQ ID NO:1 or SEQ ID NO:3.

22. An isolated nucleic acid molecule of claim 2, wherein the molecule comprises the sequence of SEQ ID NO:1, or degenerate variants thereof.

23. An isolated nucleic acid molecule of claim 2, wherein the molecule comprises the sequence of SEQ ID NO:1, or degenerate variants thereof, wherein T is replaced by U.

24. An isolated nucleic acid molecule of claim 2, wherein the molecule comprises nucleic acid sequences complementary to (a) SEQ ID NO:1 or degenerate variants thereof, or (b) SEQ ID NO:1, or degenerate variants thereof, wherein T is replaced by U.

25. An isolated nucleic acid molecule of claim 2, wherein the molecule comprises a nucleic acid that is at least 18 base pairs in length and specifically at 68° C. in 5×SSC/5× Denhardt's solution/1.0% SDS hybridizes to genomic DNA encoding the polypeptide of SEQ ID NO:2.

26. An isolated nucleic acid molecule of claim 1, wherein the nucleic acid molecule consists of the amino acid sequence of SEQ. ID NO:2.

27. An isolated nucleic acid molecule of claim 2, wherein the molecule comprises the sequence of SEQ ID NO:3, or degenerate variants thereof.

28. An isolated nucleic acid molecule of claim 2, wherein the molecule comprises the sequence of SEQ ID NO:3, or degenerate variants thereof, wherein T is replaced by U.

29. An isolated nucleic acid molecule of claim 2, wherein the molecule comprises nucleic acid sequences complementary to (a) SEQ ID NO:3 or degenerate variants thereof, or (b) SEQ ID NO:3, or degenerate variants thereof, wherein T is replaced by U.

30. An isolated nucleic acid molecule of claim 3, wherein the molecule is at least 95% identical to SEQ ID NO:1.

31. An isolated nucleic acid molecule of claim 3, wherein the molecule is identical to SEQ ID NO:1.

32. An isolated nucleic acid molecule of claim 3, wherein the molecule is at least 95% identical to SEQ ID NO:3.

33. A vector comprising a nucleic acid molecule of claim 26.

34. A vector comprising a nucleic acid molecule of claim 27.

35. A vector comprising a nucleic acid molecule of claim 3.

36. A host cell comprising an exogenously introduced nucleic acid molecule of claim 3.

37. A host cell comprising an exogenously introduced nucleic acid molecule of claim 26.

38. A host cell comprising an exogenously introduced nucleic acid molecule of claim 27.

39. A method of claim 17, wherein the nucleic acid encodes the amino acid sequence of SEQ ID NO:2.

40. A method of claim 17, wherein the nucleic acid is at least 95% identical to SEQ ID NO:1.

41. A method of claim 17, wherein the nucleic acid is at least 95% identical to SEQ ID NO: 3.

42. An isolated nucleic acid molecule of claim 20, wherein said molecule consists of the cDNA sequence contained within American Type Culture Collection (ATCC) accession number PTA-1663.

* * * * *

SEQUENCE LISTING

<160> NUMBER OF SEQ ID NOS: 10

<210> SEQ ID NO 1
<211> LENGTH: 1392
<212> TYPE: DNA
<213> ORGANISM: Aspergillus fumigatus N-myristoyl
<220> FEATURE:
<221> NAME/KEY: CDS
<222> LOCATION: (1)...(1389)

<400> SEQUENCE: 1

```
atg gcg gag tcg cta ttg gaa aac aac ccc gct ctc agg aac gag acg        48
Met Ala Glu Ser Leu Leu Glu Asn Asn Pro Ala Leu Arg Asn Glu Thr
  1               5                  10                  15 gcc ggc atg gac aaa gac aag gcg gcg gag gca atg cgc aaa atg aac        96
Ala Gly Met Asp Lys Asp Lys Ala Ala Glu Ala Met Arg Lys Met Asn
             20                  25                  30 att gcc gaa ttg ctg aca ggc ttg tca gtt tcc ggg aag aac cag aag       144
Ile Ala Glu Leu Leu Thr Gly Leu Ser Val Ser Gly Lys Asn Gln Lys
         35                  40                  45 gat atg gct tcg tac aag ttt tgg caa acg cag cct gtg ccc cga ttc       192
Asp Met Ala Ser Tyr Lys Phe Trp Gln Thr Gln Pro Val Pro Arg Phe
     50                  55                  60 gat gag acg agt acc gat act ggg ggc cct atc aag atc att gat cct       240
Asp Glu Thr Ser Thr Asp Thr Gly Gly Pro Ile Lys Ile Ile Asp Pro
 65                  70                  75                  80
```

-continued

```
gaa aag gtc tca aag gaa ccg gat gcg ctg ctt gaa gga ttt gaa tgg      288
Glu Lys Val Ser Lys Glu Pro Asp Ala Leu Leu Glu Gly Phe Glu Trp
                 85                  90                  95 gcg aca ctc gac ctg aca aac gag act gag ctg cag gag ctg tgg gat      336
Ala Thr Leu Asp Leu Thr Asn Glu Thr Glu Leu Gln Glu Leu Trp Asp
             100                 105                 110 ttg ttg acg tat cac tac gta gag gac gac aat gcc atg ttc cgg ttc      384
Leu Leu Thr Tyr His Tyr Val Glu Asp Asp Asn Ala Met Phe Arg Phe
         115                 120                 125 aga tat tcg cag tcg ttc cta cac tgg gct ctt atg tcg cct ggc tgg      432
Arg Tyr Ser Gln Ser Phe Leu His Trp Ala Leu Met Ser Pro Gly Trp
     130                 135                 140 aaa aag gaa tgg cat gtc ggt gtc cgc gct acg aag tcg cgc aaa ctg      480
Lys Lys Glu Trp His Val Gly Val Arg Ala Thr Lys Ser Arg Lys Leu
145                 150                 155                 160 gta gcg tcc att tgc ggt gtc ccg aca gag atc aat gtg cgc aat caa      528
Val Ala Ser Ile Cys Gly Val Pro Thr Glu Ile Asn Val Arg Asn Gln
                 165                 170                 175 aag ctc aag gtc gtc gag atc aat ttc ctc tgc atc cac aag aag ctc      576
Lys Leu Lys Val Val Glu Ile Asn Phe Leu Cys Ile His Lys Lys Leu
             180                 185                 190 cgc tcg aag cgc ttg acc cca gtt ctc atc aaa gaa atc acc cgt cgt      624
Arg Ser Lys Arg Leu Thr Pro Val Leu Ile Lys Glu Ile Thr Arg Arg
         195                 200                 205 tgc tac ctc aat ggc atc tac caa gcc atc tac act gcg ggt gtg gtg      672
Cys Tyr Leu Asn Gly Ile Tyr Gln Ala Ile Tyr Thr Ala Gly Val Val
     210                 215                 220 ctc ccc act cct gtc agc tca tgc cgc tac tac cac cgt cct ttg gac      720
Leu Pro Thr Pro Val Ser Ser Cys Arg Tyr Tyr His Arg Pro Leu Asp
225                 230                 235                 240 tgg ttg aag ctt tac gag gtc ggc ttc tcg cct ctc cct gcc gga tcc      768
Trp Leu Lys Leu Tyr Glu Val Gly Phe Ser Pro Leu Pro Ala Gly Ser
                 245                 250                 255 acc aag gcg cgc cag atc acc aag aat cac ctg ccc agt act acc tct      816
Thr Lys Ala Arg Gln Ile Thr Lys Asn His Leu Pro Ser Thr Thr Ser
             260                 265                 270 acc ccc ggt ctt cgc ccc atg gag ccc aaa gac att gac aca gtg cat      864
Thr Pro Gly Leu Arg Pro Met Glu Pro Lys Asp Ile Asp Thr Val His
         275                 280                 285 gat ctt ttg cag cga tac ttg tcg cgg ttt gcg ttg aac cag gcc ttt      912
Asp Leu Leu Gln Arg Tyr Leu Ser Arg Phe Ala Leu Asn Gln Ala Phe
     290                 295                 300 acg cga gag gaa gtg gac cat tgg ctc gtg cac aag ccg gag acg gtg      960
Thr Arg Glu Glu Val Asp His Trp Leu Val His Lys Pro Glu Thr Val
305                 310                 315                 320 aaa gag cag gtc gtc tgg gca tac gtg gta gag gac cct gaa acg cac     1008
Lys Glu Gln Val Val Trp Ala Tyr Val Val Glu Asp Pro Glu Thr His
                 325                 330                 335 aag atc acc gac ttc ttt tcc ttc tac aac ctc gaa tcc acc gtc att     1056
Lys Ile Thr Asp Phe Phe Ser Phe Tyr Asn Leu Glu Ser Thr Val Ile
             340                 345                 350 cag aat ccc aag cat gac aat gtg cgt gct gct tac ctg tac tac tat     1104
Gln Asn Pro Lys His Asp Asn Val Arg Ala Ala Tyr Leu Tyr Tyr Tyr
         355                 360                 365 gca acc gaa aca gct ttc acc aat aac atg aag gct ctc aaa gag cgt     1152
Ala Thr Glu Thr Ala Phe Thr Asn Asn Met Lys Ala Leu Lys Glu Arg
     370                 375                 380 ctg ctg atg ctg atg aat gac gct ctg atc ctg gct aag aag gcg cac     1200
Leu Leu Met Leu Met Asn Asp Ala Leu Ile Leu Ala Lys Lys Ala His
```

```
                385                 390                 395                 400
ttt gat gtg ttc aac gca ctt acg ctt cac gat aac cct ctg ttc ctc           1248
Phe Asp Val Phe Asn Ala Leu Thr Leu His Asp Asn Pro Leu Phe Leu
            405                 410                 415 gaa caa ctc aaa ttt gga gct ggc gat ggg cag ctt cac ttc tac ctc           1296
Glu Gln Leu Lys Phe Gly Ala Gly Asp Gly Gln Leu His Phe Tyr Leu
            420                 425                 430 tac aac tat cgc acc gcc cct gtt cct gga gga gtt aac gag aag aac           1344
Tyr Asn Tyr Arg Thr Ala Pro Val Pro Gly Gly Val Asn Glu Lys Asn
            435                 440                 445 ctg ccg gat gag aaa aga atg gga ggc gtt ggc atc gtt atg ctg               1389
Leu Pro Asp Glu Lys Arg Met Gly Gly Val Gly Ile Val Met Leu
    450                 455                 460 taa                                                                       1392
```

<210> SEQ ID NO 2
<211> LENGTH: 463
<212> TYPE: PRT
<213> ORGANISM: Aspergillus fumigatus N-myristoyl

<400> SEQUENCE: 2

```
Met Ala Glu Ser Leu Leu Glu Asn Asn Pro Ala Leu Arg Asn Glu Thr
 1               5                  10                  15

Ala Gly Met Asp Lys Asp Lys Ala Ala Glu Ala Met Arg Lys Met Asn
            20                  25                  30

Ile Ala Glu Leu Leu Thr Gly Leu Ser Val Ser Gly Lys Asn Gln Lys
        35                  40                  45

Asp Met Ala Ser Tyr Lys Phe Trp Gln Thr Gln Pro Val Pro Arg Phe
    50                  55                  60

Asp Glu Thr Ser Thr Asp Thr Gly Gly Pro Ile Lys Ile Asp Pro
 65                  70                  75                  80

Glu Lys Val Ser Lys Glu Pro Asp Ala Leu Leu Glu Gly Phe Glu Trp
                85                  90                  95

Ala Thr Leu Asp Leu Thr Asn Glu Thr Glu Leu Gln Glu Leu Trp Asp
            100                 105                 110

Leu Leu Thr Tyr His Tyr Val Glu Asp Asp Asn Ala Met Phe Arg Phe
        115                 120                 125

Arg Tyr Ser Gln Ser Phe Leu His Trp Ala Leu Met Ser Pro Gly Trp
    130                 135                 140

Lys Lys Glu Trp His Val Gly Val Arg Ala Thr Lys Ser Arg Lys Leu
145                 150                 155                 160

Val Ala Ser Ile Cys Gly Val Pro Thr Glu Ile Asn Val Arg Asn Gln
                165                 170                 175

Lys Leu Lys Val Val Glu Ile Asn Phe Leu Cys Ile His Lys Lys Leu
            180                 185                 190

Arg Ser Lys Arg Leu Thr Pro Val Leu Ile Lys Glu Ile Thr Arg Arg
        195                 200                 205

Cys Tyr Leu Asn Gly Ile Tyr Gln Ala Ile Tyr Thr Ala Gly Val Val
    210                 215                 220

Leu Pro Thr Pro Val Ser Ser Cys Arg Tyr Tyr His Arg Pro Leu Asp
225                 230                 235                 240

Trp Leu Lys Leu Tyr Glu Val Gly Phe Ser Pro Leu Pro Ala Gly Ser
                245                 250                 255

Thr Lys Ala Arg Gln Ile Thr Lys Asn His Leu Pro Ser Thr Thr Ser
            260                 265                 270
```

-continued

```
Thr Pro Gly Leu Arg Pro Met Glu Pro Lys Asp Ile Asp Thr Val His
            275                 280                 285

Asp Leu Leu Gln Arg Tyr Leu Ser Arg Phe Ala Leu Asn Gln Ala Phe
        290                 295                 300

Thr Arg Glu Glu Val Asp His Trp Leu Val His Lys Pro Glu Thr Val
305                 310                 315                 320

Lys Glu Gln Val Val Trp Ala Tyr Val Val Glu Asp Pro Glu Thr His
                325                 330                 335

Lys Ile Thr Asp Phe Phe Ser Phe Tyr Asn Leu Glu Ser Thr Val Ile
            340                 345                 350

Gln Asn Pro Lys His Asp Asn Val Arg Ala Ala Tyr Leu Tyr Tyr Tyr
        355                 360                 365

Ala Thr Glu Thr Ala Phe Thr Asn Asn Met Lys Ala Leu Lys Glu Arg
    370                 375                 380

Leu Leu Met Leu Met Asn Asp Ala Leu Ile Leu Ala Lys Lys Ala His
385                 390                 395                 400

Phe Asp Val Phe Asn Ala Leu Thr Leu His Asp Asn Pro Leu Phe Leu
                405                 410                 415

Glu Gln Leu Lys Phe Gly Ala Gly Asp Gly Gln Leu His Phe Tyr Leu
            420                 425                 430

Tyr Asn Tyr Arg Thr Ala Pro Val Pro Gly Gly Val Asn Glu Lys Asn
        435                 440                 445

Leu Pro Asp Glu Lys Arg Met Gly Gly Val Gly Ile Val Met Leu
    450                 455                 460

<210> SEQ ID NO 3
<211> LENGTH: 1735
<212> TYPE: DNA
<213> ORGANISM: Aspergillus fumigatus N-myristoyl

<400> SEQUENCE: 3
tccgactcta aggatcgcaa gggcaaggcc cccgagggcc agtcttccga aaagaaagat      60
ggcgcggtga acataacccc tcagatggcg gagtcgctat tggaaaacaa ccccgctctc    120
aggaacgaga cggccggcat ggacaaagac aaggcggcgg aggcaatgcg caaaatgaac    180
attgccgaat tgctgacagg cttgtcagtt tccgggaaga accagaagga tatggcttcg    240
tacaagtttt ggcaaacgca gcctgtgccc cgattcgatg agacgagtac cgatactggg    300
ggccctatca agatcattga tcctgaaaag gtctcaaagg aaccggatgc gctgcttgaa    360
ggatttgaat gggcgacact cgacctgaca aacgagactg agctgcagga gctgtgggat    420 tgttgacgt atcactacgt agaggacgac aatgccatgt tccggttcag atattcgcag    480
tcgttcctac actggtgggt gcacaacgcg gccgagggat ctgtttctca ccggcttggg    540
agggtgtgga ttatttgagc gctgacaatt ttgaccgtag ggctcttatg tcgcctggct    600
ggaaaaagga atggcatgtc ggtgtccgcg ctacgaagtc gcgcaaactg gtagcgtcca    660
tttgcggtgt cccgacagag atcaatgtgc gcaatcaaaa gctcaaggtc gtcgagatca    720
atttcctctg catccacaag aagctccgct cgaagcgctt gaccccagtt ctcatcaaag    780
aaatcacccg tcgttgctac ctcaatggca tctaccaagc catctacact gcgggtgtgg    840
tgctccccac tcctgtcagc tcatgccgct actaccaccg tcctttggac tggttgaagc    900
tttacgaggt cggcttctcg cctctccctg ccggatccac caaggcgcgc cagatcacca    960
agaatcacct gcccagtact acctctaccc ccggtcttcg ccccatggag cccaaagaca   1020
ttgacacagt gcatgatctt ttgcagcgat acttgtcgcg gtttgcgttg aaccaggcct   1080
```

```
ttacgcgaga ggaagtggac cattggctcg tgcacaagcc ggagacggtg aaagagcagg    1140
tcgtctgggc atacgtggta gaggaccctg aaacgcacaa gatcaccgac ttcttttcct    1200
tctacaacct cgaatccacc gtcattcaga atcccaagca tgacaatgtg cgtgctgctt    1260
acctgtacta ctatgcaacc gaaacagctt tcaccaataa catgaaggct ctcaaagagc    1320
gtctgctgat gctgatgaat gacgctctga tcctggctaa gaaggtaact acagggatcc    1380
actgccattt ccctggagtt gacttacgaa gctgacattg tgttgatagg cgcactttga    1440
tgtgttcaac gcacttacgc ttcacgataa ccctctgttc ctcgaacaac tcaaatttgg    1500
agctggcgat gggcagcttc acttctacct ctacaactat cgcaccgccc ctgttcctgg    1560
aggagttaac gagaagaacc tgccggatga gaaaagaatg ggaggcgttg gcatcgttat    1620
gctgtaaaac attctcaccg catggaccat gcctctcgcc tcgttgatga tcgcatctta    1680
tacctatttc tcgctgtgac atgaatttgg gtatgcgaaa taccatgaaa atttg         1735
```

<210> SEQ ID NO 4
<211> LENGTH: 17
<212> TYPE: DNA
<213> ORGANISM: Aspergillus fumigatus N-myristoyl
<220> FEATURE:
<221> NAME/KEY: misc_feature
<222> LOCATION: (1)...(17)
<223> OTHER INFORMATION: n = A,T,C or G

<400> SEQUENCE: 4
ranmaytayg tngarga                                                   17

<210> SEQ ID NO 5
<211> LENGTH: 20
<212> TYPE: DNA
<213> ORGANISM: Aspergillus fumigatus N-myristoyl
<220> FEATURE:
<221> NAME/KEY: misc_feature
<222> LOCATION: (1)...(20)
<223> OTHER INFORMATION: n = A,T,C or G

<400> SEQUENCE: 5
canarraart tdatytcnac                                                20

<210> SEQ ID NO 6
<211> LENGTH: 19
<212> TYPE: DNA
<213> ORGANISM: Aspergillus fumigatus N-myristoyl

<400> SEQUENCE: 6
tgccatcttc cggttcaga                                                 19

<210> SEQ ID NO 7
<211> LENGTH: 21
<212> TYPE: DNA
<213> ORGANISM: Aspergillus fumigatus N-myristoyl

<400> SEQUENCE: 7
tgcgcgactt cgtaggcggg a                                              21

<210> SEQ ID NO 8
<211> LENGTH: 39
<212> TYPE: DNA
<213> ORGANISM: Aspergillus fumigatus N-myristoyl

<400> SEQUENCE: 8

```
cgcgcatatg gcggagtcgc tattggaaaa caaccccgc                      39

<210> SEQ ID NO 9
<211> LENGTH: 39
<212> TYPE: DNA
<213> ORGANISM: Aspergillus fumigatus N-myristoyl

<400> SEQUENCE: 9
gcagcggccg cttacagcat aacgatgcca acgcctgcc                      39

<210> SEQ ID NO 10
<211> LENGTH: 1735
<212> TYPE: DNA
<213> ORGANISM: Aspergillus fumigatus N-myristoyl

<400> SEQUENCE: 10
aggctgagat tcctagcgtt cccgttccgg gggctcccgg tcagaaggct tttctttcta    60
ccgcgccact tgtattgggg agtctaccgc ctcagcgata accttttgtt ggggcgagag   120
tccttgctct gccggccgta cctgtttctg ttccgccgcc tccgttacgc gttttacttg   180
taacggctta cgactgtcc  gaacagtcaa aggcccttct tggtcttcct ataccgaagc   240
atgttcaaaa ccgtttgcgt cggacacggg gctaagctac tctgctcatg gctatgaccc   300
ccgggatagt tctagtaact aggactttc  cagagtttcc ttggcctacg cgacgaactt   360
cctaaactta cccgctgtga gctggactgt ttgctctgac tcgacgtcct cgacaccctcta 420
aacaactgca tagtgatgca tctcctgctg ttacggtaca aggccaagtc tataagcgtc   480
agcaaggatg tgaccaccca cgtgttgcgc cggctcccta gacaaagagt ggccgaaccc   540
tcccacacct aataaactcg cgactgttaa aactggcatc ccgagaatac agcggaccga   600
ccttttcct  taccgtacag ccacaggcgc gatgcttcag cgcgtttgac catcgcaggt   660
aaacgccaca gggctgtctc tagttacacg cgttagtttt cgagttccag cagctctagt   720
taaaggagac gtaggtgttc ttcgaggcga gcttcgcgaa ctggggtcaa gagtagtttc   780
tttagtgggc agcaacgatg gagttaccgt agatggttcg gtagatgtga cgcccacacc   840
acgaggggtg aggacagtcg agtacggcga tgatggtggc aggaaacctg accaacttcg   900
aaatgctcca gccgaagagc ggagagggac ggcctaggtg gttccgcgcg gtctagtggt   960
tcttagtgga cgggtcatga tggagatggg ggccagaagc ggggtacctc gggtttctgt  1020
aactgtgtca cgtactagaa aacgtcgcta tgaacagcgc caaacgcaac ttggtccgga  1080
aatgcgctct ccttcacctg gtaaccgagc acgtgttcgg cctctgccac tttctcgtcc  1140
agcagacccg tatgcaccat ctcctgggac tttgcgtgtt ctagtggctg aagaaaagga  1200
agatgttgga gcttaggtgg cagtaagtct tagggttcgt actgttacac gcacgacgaa  1260
tggacatgat gatacgttgg cttgtcgaa  agtggttatt gtacttccga gagtttctcg  1320
cagacgacta cgactactta cagcgagact aggaccgatt cttccattga tgtccctagg  1380
tgacggtaaa gggaccctcaa ctgaatgctt cgactgtaac acaactatcc gcgtgaaact  1440
acacaagttg cgtgaatgcg aagtgctatt gggagacaag gagcttgttg agtttaaacc  1500
tcgaccgcta cccgtcgaag tgaagatgga gatgttgata gcgtggcggg gacaaggacc  1560
tcctcaattg ctcttcttgg acggcctact cttttcttac cctccgcaac cgtagcaata  1620
cgacattttg taagagtggc gtacctggta cggagagcgg agcaactact agcgtagaat  1680
atggataaag agcgacactg tacttaaacc catacgcttt atggtacttt taaac        1735
```